United States Patent [19]

Geadelmann et al.

[11] Patent Number: 5,750,851
[45] Date of Patent: May 12, 1998

US005750851A

[54] INBRED CORN LINE QH101

[75] Inventors: Jon L. Geadelmann, Roseville, Minn.; Kenneth Leto, West Des Moines, Iowa

[73] Assignee: E I Dupont de Nemours and Company, Wilmington, Del.

[21] Appl. No.: 759,735

[22] Filed: Dec. 6, 1996

[51] Int. Cl.$^6$ ............... A01H 5/00; A01H 4/00; A01H 1/00; C12N 5/04

[52] U.S. Cl. ............ 800/200; 800/250; 800/DIG. 56; 47/58; 47/DIG. 1; 435/412; 435/424; 435/430; 435/430.1

[58] Field of Search ............... 800/200, 205, 800/250, DIG. 56; 47/58, DIG. 1; 435/172.1, 172.3, 412, 424, 430, 430.1

[56] References Cited

PUBLICATIONS

Phillips et al. "Cell/Tissue Culture and Invitro Manipulation" In COrn and Corn Improvement, ASA Pub #18, 3rd edition pagfe 358, 1988.

Plant Variety Protection Certificate for Inbred Corn Line LH51 Jun. 1983.

*Primary Examiner*—Gary Benzion
*Attorney, Agent, or Firm*—Rothwell, Figg, Ernst & Kurz, pc

[57] ABSTRACT

An inbred corn line, designated QH101, is disclosed. The invention relates to the seeds of inbred corn line QH101, to the plants of inbred corn line QH101 and to methods for producing a corn plant produced by crossing the inbred line QH101 with itself or another corn line. The invention further relates to hybrid corn seeds and plants produced by crossing the inbred line QH101 with another corn line.

10 Claims, No Drawings

INBRED CORN LINE QH101

BACKGROUND OF THE INVENTION

The present invention relates to a new and distinctive corn inbred line, designated QH101. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits. Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987). Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock. Corn is an important and valuable field crop. Thus, a continuing goal of plant breeders is to develop stable, high yielding corn hybrids that are agronomically sound. The reasons for this goal are obviously to maximize the amount of grain produced on the land used and to supply food for both animals and humans. To accomplish this goal, the corn breeder must select and develop corn plants that have the traits that result in superior parental lines for producing hybrids.

SUMMARY OF THE INVENTION

According to the invention, there is provided a novel inbred corn line, designated QH101. This invention thus relates to the seeds of inbred corn line QH101, to the plants of inbred corn line QH101 and to methods for producing a corn plant produced by crossing the inbred line QH101 with itself or another corn line. This invention further relates to hybrid corn seeds and plants produced by crossing the inbred line QH101 with another corn line.

DEFINITIONS

In the description and tables which follow, a number of terms are used. In order to provide a clear and consistent understanding of the specification and claims, including the scope to be given such terms, the following definitions are provided:

Predicted RM. This trait for a hybrid, predicted relative maturity (RM), is based on the harvest moisture of the grain. The relative maturity rating is based on a known set of checks and utilizes conventional maturity systems such as the Minnesota Relative Maturity Rating System.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Yield (Bushels/Acre). The yield in bushels/acre is the actual yield of the grain at harvest adjusted to 15.5% moisture.

Moisture. The moisture is the actual percentage moisture of the grain at harvest.

GDU Silk. The GDU silk (=heat unit silk) is the number of growing degree units (GDU) or heat units required for an inbred line or hybrid to reach silk emergence from the time of planting. Growing degree units are calculated by the Barger Method, where the heat units for a 24-hour period are:

$$GDU = \frac{(Max. + Min)}{2} - 50.$$

The highest maximum used is 86° F. and the lowest minimum used is 50° F. For each hybrid, it takes a certain number of GDUs to reach various stages of plant development. GDUs are a way of measuring plant maturity.

Stalk Lodging. This is the percentage of plants that stalk lodge, i.e., stalk breakage, as measured by either natural lodging or pushing the stalks determining the percentage of plants that break off below the ear. This is a relative rating of a hybrid to other hybrids for standability.

Root Lodging. The root lodging is the percentage of plants that root lodge; i.e., those that lean from the vertical axis at an approximate 30° angle or greater would be counted as root lodged.

Plant Height. This is a measure of the height of the hybrid from the ground to the tip of the tassel, and is measured in centimeters.

Ear Height. The ear height is a measure from the ground to the ear node attachment, and is measured in centimeters.

Dropped Ears. This is a measure of the number of dropped ears per plot, and represents the percentage of plants that dropped an ear prior to harvest.

DETAILED DESCRIPTION OF THE INVENTION

Inbred corn line QH101 is a yellow dent corn with superior characteristics, and provides an excellent parental line in crosses for producing first generation ($F_1$) hybrid corn.

The development of QH101 was initiated by crossing LH51wx/wx with UHOC3-341. The resulting single cross was then backcrossed with LH51wx. Yield, stalk quality, root quality, disease tolerance, late plant greenness, late plant intactness, ear retention, pollen shedding ability, silking ability and corn borer tolerance were the criteria used to determine the rows from which ears were selected.

The widespread demand for high oil corn to meet the needs of poultry, swine, dairy and beef producers is increasingly being met by commercial acceptance of the TopCross® grain production system (WO 92/08314 published 29 May 1992). The TopCross® system is a novel method for the commercial production of corn grain containing enhanced quality grain traits. Application of the method results in the production of grain with an enhanced oil content following the pollination of high yielding, male sterile plants by plants containing genes for high oil content. The pollinator plants with high oil content need not be genetically homozygous (inbred) or even homogeneous in appearance, may not be high yielding, and are not selected for combining ability with high yielding female plants. As a consequence the breeding time line for the production of commercially successful pollinators with a high oil content is significantly and dramatically reduced. Further, many existing male sterile corn hybrids may be used directly in the TopCross® grain production system without the need to introduce high oil genes into the male sterile hybrids themselves. Taken together, the rapid production of high oil pollinators and the immediate availability of high yielding male sterile corn hybrids has greatly accelerated the commercial production of high oil corn grain. The TopCross® grain production method has catalyzed a great expansion in the number of available agronomically elite, high yielding plants which can be used to produce grain with a high oil content, thus increasing both the yield and the production range of corn varieties bearing grain with a high oil content.

Because of it's high oil content QH101 may be suitable for use as a pollinator in the TopCross® production system. Most likely, QH101 would be used in combination with other high oil materials to create a high oil corn variety which would possess sufficient oil to produce high oil corn grain when employed in the TopCross® grain production system. As one example, QH101 might be combined with a second non-homogeneous high oil corn variety to produce a nonuniform hybrid variety suitable as a pollinator. As a second example, QH101 might be combined with two or more high oil corn varieties to produce a 3-way cross hybrid corn plant suitable for use as a hybrid pollinator. As a general case, QH101 might be combined with a number of other high and low oil materials to produce any number of corn varieties with a composite oil content high enough to serve as a high oil pollinator in the TopCross® grain production system.

Inbred corn line QH101 has the following morphologic and other characteristics (based primarily on data collected at Williamsburg, Iowa).

VARIETY DESCRIPTION INFORMATION

1. TYPE: Dent
2. REGION WHERE DEVELOPED: Northcentral U.S.
3. MATURITY:

|  | Days | Heat Units |
|---|---|---|
| From emergence to 50% of plants in silk: | 91 | 1558 |
| From emergence to 50% of plants in pollen | 90 | 1535 |

$$\text{Heat Units:} = \frac{[\text{Max. Temp.} (\leq 86° \text{F.}) + \text{Min. Temp.} (>50° \text{F.})]}{2} - 50$$

4. PLANT:

Plant Height (to tassel tip): 189.0 cm (SD=9.70)
Ear Height (to base of top ear): 74.3 cm (7.81)
Average Length of Top Ear Internode: 15.4 cm (1.70)
Average number of Tillers: 0 (0)
Average Number of Ears per Stalk: 1.0 (0.0)
Anthocyanin of Brace Roots: Absent

5. LEAF:

Width of Ear Node Leaf: 8.8 cm (0.86)
Length of Ear Node Leaf: 61.6 cm (4.05)
Number of leaves above top ear: 5 (0.47)
Leaf Angle from 2nd Leaf above ear at anthesis to Stalk above leaf: 24° (6.66)
Leaf Color: Medium Green—Munsell Code 5 GY 4/4
Leaf Sheath Pubescence (Rate on scale from 1=none to 9=like peach fuzz): 3
Marginal Waves (Rate on scale from 1=none to 9=many): 9
Longitudinal Creases (Rate on scale from 1=none to 9=many): 6

6. TASSEL:

Number of Lateral Branches: 9 (1.32)
Branch Angle from Central Spike: 22 (11.85)
Tassel Length (from top leaf collar to tassel top): 41.7 cm (3.50)
Pollen Shed (Rate on scale from 0=male sterile to 9=heavy shed): 6
Anther Color: Purple—Munsell Code 5RP 5/8
Glume Color: Medium Green—Munsell Code 5GY 5/6
Bar Glumes: Absent 7a. EAR: (Unhusked Data)

Silk Color (3 days after emergency): Dark Salmon—Munsell Code 5Y 5/6
Fresh Husk Color (25 days after 50% silking): Light Green—Munsell Code 2.5GY 7/6
Dry Husk Color (65 days after 50% silking): Buff—Munsell Code 7.5YB 7/4
Position of Ear: Pendent
Husk Tightness (Rate on scale from 1=very loose to 9=very tight): 7
Husk Extension: Medium (<8 cm beyond ear tip)

7b. EAR: (Husked Ear Data)

Ear Length: 15.0 cm (1.19)
Ear Diameter at mid-point: 34.6 mm (2.40)
Ear Weight: 59.0 gm (14.23)
Number of Kernel Rows: 10 (1.45)
Kernel Rows: Distinct
Row Alignment: Straight
Shank Length: 10.3 cm (3.37)
Ear Taper: Average 8. KERNEL: (Dried)

Kernel Length: 9.4 mm (0.64)
Kernel Width: 7.3 mm (0.54)
Kernel Thickness: 4.6 mm (0.61)
Round Kernels (Shape Grade): 33.7% (6.13)
Aleurone Color Pattern: Homozygous
Aleurone Color: White
Hard Endosperm Color: Pale Yellow (Munsell code 2.5Y 8/10)
Endosperm Type: Waxy Starch—High Oil
Weight per 100 kernels (unsized sample): 20.2 gm (0.42)

9. COB:

Cob Diameter at Mid-Point: 27.8 mm (2.50)
Cob Color: Red (Munsell code 1OR 4/6)

10. AGRONOMIC TRAITS:

2 Stay Green (at 65 days after anthesis) (Rate on scale from 1=worst to 9=excellent)
0% Dropped Ears (at 65 days after anthesis)
0% Pre-anthesis Brittle Snapping
0% Pre-anthesis Root Lodging
0% Post-anthesis Root Lodging (at 65 days after anthesis)

This invention is also directed to methods for producing a corn plant by crossing a first parent corn plant with a second parent corn plant, wherein the first or second corn plant is the inbred corn plant from the line QH101. Further, both first and second parent corn plants may be from the inbred line QH101. Therefore, any methods using the inbred corn line QH101 are part of this invention: selfing, backcrosses, hybrid breeding, and crosses to populations. Any plants produced using inbred corn line QH101 as a parent are within the scope of this invention. Advantageously, the inbred corn line is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like. Tissue culture of corn is described in European Patent Application, Publication No. 160,390, incorporated herein by reference. Corn tissue culture procedures are also described in Green and Rhodes, "Plant Regeneration in Tissue Culture of Maize", Maize for Biological Research (Plant Molecular Biology Association, Charlottesville, Va. 1982), at 367–372. Thus, another aspect of this invention is to provide for cells which upon growth and differentiation produce the inbred line QH101.

LH51wx, one of the progenitors of QH101, is a proprietary field corn inbred line of Holden's Foundation Seeds, Inc. of Williamsburg, Iowa and protected by a plant variety certificate #8200062 on Jun. 30, 1983. UHO (Ultra High Oil) is a high oil corn population developed by the University of Illinois. This particular selection, UHOC3-41, is included in a license agreement between the University of Illinois and the joint venture collaboration of E.I. DuPont De Nemours & Co. Of Wilmington, Del. and Pfister Hybrid Corn Co. Of El Paso, Ill.

QH101 is most similar to LH51, however, there are numerous differences. One distinguishing difference is the composition of the kernel. The kernel composition of QH101 is higher in amylopectin (waxy) content and higher in oil content than the kernel of LH51 which is a normal dent corn inbred. The number and the distinctness of the marginal waves on the leaves of QH101 is much more noticeable than on the leaves of LH51. The leaves of QH101 exhibit a very wrinkled appearance from the midrib to the margin. The leaves of LH51 do display marginal waves, however, they are present on the leaf margin located on the outer edge of the leaf and the leaf does not have the wrinkled appearance at the middle of the leaf toward the midrib. This trait is genetic and not an environmental or chemical interaction as it has been observed at a number of different locations.

QH101 is a medium late early season, high oil, waxy corn inbred. It is a very good pollinator, but is not suitable for use as a seed parent. QH101 flowers approximately 4 days earlier than LH51.

The collaborating companies define high oil corn as corn that contains at least 6% oil on a dry matter basis, as compared to normal corn that contains about 4% oil. Another way to define it is to say that high oil corn must provide at least 2100 Kcal/lb of gross energy, compared with the value of 2040 Kcal/lb for normal corn. Oil has twice as much energy as starch, on a per unit weight basis, so high oil corn has more nutrient or caloric density than regular corn. This higher caloric density offers benefits to the livestock producer in two ways: 1) It can substitute for fat already being added to optimized rations; or 2) it can add energy to rations already being optimized. The higher caloric density means animals will get more growth or production energy for any given volume of feed consumed. High oil corn also offers a better amino acid balance than normal corn, with somewhat higher levels of lysine and methionine. In operations where dust levels are a problem (feed mills, confinement facilities, etc.) high oil corn offers the additional advantage of low dust, eliminating the ned for spraying with water or vegetable oil to reduce dust.

QH101, when crossed with a normal corn inbred, appears to contribute oil levels to the grain of its hybrids in the range of 6.25%–6.75% (dry basis) in a "typical" year. In 1995, LH195×QH101 and LH200×QH101 expressed good plant health and standability and yielded within 6 bushels per acre of the LH51 and LH216 standard hybrids, with approximately 0.7% more harvest grain moisture.

The fact that QH101 is waxy as well as high oil may be interesting in some applications. Grain from waxy hybrids is typically a few tenths of a point higher in oil than corresponding normal hybrid grain, but also approximately a half percent wetter in harvest moisture. There is a possible use for high oil, waxy corn products in dairy cow feed rations. When a non-waxy inbred is used in combination with QH101 to make a hybrid, the grain produced in the farmer's field will actually segregate and one quarter of the kernels will be waxy.

Some of the criteria used to select ears in various generations include: yield, stalk quality, root quality, disease tolerance, late plant greenness, late season plant intactness, ear retention, pollen shedding ability, silking ability, and corn borer tolerance. During the development of the line, crosses were made to inbred testers for the purpose of estimating the line's general and specific combining ability, and evaluations were run by the Williamsburg, Iowa Research Station. The inbred was evaluated further as a line and in numerous crosses by the Williamsburg and other research stations across the Corn Belt. The inbred has proven to have a very good combining ability in hybrid combinations.

The inbred has shown uniformity and stability for all traits. It has been self-pollinated and ear-rowed a sufficient number of generations, with careful attention to uniformity of plant type to ensure homozygosity and phenotypic stability. The line has been increased both by hand and sibbed in isolated fields with continued observations for uniformity. No variant traits have been observed or are expected in QH101.

TABLES

In the tables that follow, the traits and characteristics of inbred corn line QH101 are given in hybrid combination. The data collected on inbred corn line QH101 is presented for the key characteristics and traits. The tables present yield test information about QH101. QH101 was tested in several hybrid combinations at numerous locations, with two or three replications per location. Information about these hybrids, as compared to several check hybrids, is presented.

The first pedigree listed in the comparison group is the hybrid containing QH101. Information for the pedigree includes:

1. Average Oil A mean for the average oil for the hybrid across all locations.
2. Mean yield of the hybrid across all locations.
3. A mean for the percentage moisture (% M) for the hybrid across all locations.
4. A mean of the yield divided by the percentage moisture (Y/M) for the hybrid across all locations.
5. A mean of the percentage of plants with stalk lodging (% Stalk) across all locations.

6. A mean of the percentage of plants with root lodging (% Root) across all locations.
7. A mean of the percentage of plants with dropped ears (% Drop).
8. The number of locations indicates the locations where these hybrids were tested together.

The series of hybrids listed under the hybrid containing QH101 are considered check hybrids. The check hybrids are compared to hybrids containing the inbred QH101.

The (+) or (−) sign in front of each number in each of the columns indicates how the mean values across plots of the hybrid containing inbred QH101 compare to the check crosses. A (+) or (−) sign in front of the number indicates that the mean of the hybrid containing inbred QH101 was greater or lesser, respectively, than the mean of the check hybrid. For example, a +4 in yield signifies that the hybrid containing inbred QH101 produced 4 bushels more corn than the check hybrid. If the value of the stalks has a (−) in front of the number 2, for example, then the hybrid containing the inbred QH101 had 2% less stalk lodging than the check hybrid.

TABLE 1

OVERALL COMPARISONS
LH195 X QH101 HYBRID VERSUS CHECK HYBRIDS

| Hybrid | Avg Oil | Mean Yield | % M | Y/M | % Stalk | % Root | % Drop | Plant Hgt | Ear Hgt |
|---|---|---|---|---|---|---|---|---|---|
| LH195 x QH101 (at 12 Locations) As Compared To: | 5.8 | 148 | 22.35 | 6.63 | 4 | 0 | 1 | 108 | 53 |
| LH200 x LP26 | | +10 | −2.30 | +1.04 | +1 | 0 | 0 | +5 | +7 |
| LH192 x LP11 | | +19 | −.12 | +.88 | +1 | −1 | +1 | +8 | +6 |
| LH195 x LP11 | | +15 | +.23 | +.60 | +1 | 0 | +1 | +6 | +7 |
| LH195 x LH51 | | −3 | +.60 | −.33 | +2 | 0 | 0 | −5 | −3 |
| LH200 x LH216 | | −5 | +.97 | −.56 | +2 | 0 | +1 | −1 | 0 |

TABLE 2

OVERALL COMPARISONS
LH200 X QH101 HYBRID VERSUS CHECK HYBRIDS

| Hybrid | Avg Oil | Mean Yield | % M | Y/M | % Stalk | % Root | % Drop | Plant Hgt | Ear Hgt |
|---|---|---|---|---|---|---|---|---|---|
| LH200 x QH101 (at 12 Locations) As Compared To: | 5.6 | 151 | 21.55 | 7.02 | 7 | 0 | 0 | 108 | 55 |
| LH200 x LP26 | | +14 | −3.10 | +1.44 | +4 | 0 | 0 | +6 | +9 |
| LH192 x LP11 | | +22 | −.92 | +1.27 | +4 | −1 | 0 | +8 | +8 |
| LH195 x LP11 | | +18 | −.57 | +1.00 | +3 | 0 | 0 | +7 | +9 |
| LH195 x LH51 | | 0 | −.20 | +.07 | +4 | 0 | 0 | −5 | −1 |
| LH200 x LH216 | | −2 | +.17 | −.16 | +5 | 0 | 0 | 0 | +2 |

TABLE 3

OVERALL COMPARISONS
LH199 X QH101 HYBRID VERSUS CHECK HYBRIDS

| Hybrid | Avg Oil | Mean Yield | % M | Y/M | % Stalk | % Root | % Drop | Plant Hgt | Ear Hgt |
|---|---|---|---|---|---|---|---|---|---|
| LH199 x QH101 (at 14 Locations) As Compared To: | 5.9 | 152 | 23.94 | 6.36 | 1 | 0 | 0 | 105 | 48 |
| LH200 x LP26 | | +8 | −2.96 | +.98 | 0 | −3 | −0 | +6 | +6 |
| LH192 x LP11 | | +23 | −1.40 | +1.25 | 0 | −2 | 0 | −1 | +6 |
| LH199 x LP11 | | +22 | −.12 | +.96 | 0 | −1 | 0 | −6 | +3 |
| LH192 x LH82 | | −2 | +1.71 | −.57 | 0 | −1 | 0 | +8 | +10 |
| LH199 x LH216 | | +5 | +2.27 | −.44 | +1 | −1 | 0 | −7 | +5 |
| LH199 x LH218 | | +3 | +2.54 | −.63 | 0 | 0 | 0 | 0 | +4 |

TABLE 4

OVERALL COMPARISONS
LH198 X QH101 HYBRID VERSUS CHECK HYBRIDS

| Hybrid | Avg Oil | Mean Yield | % M | Y/M | % Stalk | % Root | % Drop | Plant Hgt | Ear Hgt |
|---|---|---|---|---|---|---|---|---|---|
| LH198 x QH101 (at 13 Locations) As compared to: | 5.6 | 143 | 20.01 | 7.16 | 4 | 1 | 1 | 112 | 49 |
| LH119wx x LH82wx |  | +3 | −1.13 | +.55 | +1 | 0 | +1 | +14 | +13 |
| Pfister Brand |  | +8 | −.28 | +.52 | 0 | −3 | 0 | −6 | 0 |
| LH198 x LH216 |  | −11 | +1.14 | −1.01 | +2 | −1 | 0 | +2 | −3 |
| LH198 x LP11 |  | +6 | +1.21 | −.14 | −1 | −1 | 0 | +2 | +4 |
| LH198 x LH185 |  | −15 | +1.76 | −1.50 | +1 | −2 | 0 | −4 | +2 |
| LH231 x LH172 |  | +10 | +2.50 | −.51 | +2 | 0 | 0 | +17 | +10 |

EXAMPLE 1

QH101 Used to Create Pollinator Corn Plants Which Will Increase the Oil Content of Grain in the Topcross® Grain Production System The following example demonstrates that QH101 can be combined with other corn varieties to produce a corn plant which, when used as a pollinator, can produce corn grain which is high in oil on hybrid corn plants. As shown in Table 1, corn plants were grown in nurseries at two locations in Williamsburg, Iowa ($IA_1$ and $IA_2$) or in Franklin, Ind. (IN) during the summer of 1996. In each case, pollen was collected from high oil corn plants used as pollinators and was transferred to the silks of hybrid corn plants by hand pollination methods well known to the breeder's art. Prior to and following this pollination, silks were kept covered to exclude foreign pollen. The kernels arising on the ears born on these hybrid corn plants were shelled, packaged, and sent to the DuPont Optimum Quality Grain Laboratory in Des Moines, Iowa for analysis. Corn grain was analyzed for it's oil content by near infrared transmission spectrophotometry on instruments previously calibrated to report the oil content of the grain on a weight percent dry matter basis as shown in Table 1. For any given pollinator and hybrid combination, the composition of the grain produced by hand pollinated nurseries is predictive of the composition of grain produced by that pollinator and a corresponding grain parent (e.g. a male sterile version of that hybrid) in the TopCross® grain production system (WO 92/08314 published 29 May 1992).

In this example, varieties designated "ZX", "QH101" and "P22" all possess high oil. All hybrids designated "LH" possess low oil contents typical of field corn commonly grown in the United States corn belt. Oil measurements were taken on the grain arising on the female corn variety (listed first) by the male or pollinator corn variety (listed second), which is listed by convention in Table 1 as: female parent) (male parent

| Location | Pedigree | % Oil (db) |
|---|---|---|
|  | Low Oil Hybrid x QH101 High Oil Hybrids |  |
| IA1 | LH192SDms x LH82)(Zx1 x QH101 | 6.92 |
| IA1 | LH192SDms x LH82)(Zx15 x QH101 | 6.22 |
| IA1 | LH192SDms x LH82)(Zx2 x QH101 | 6.79 |
| IA1 | LH192Dms x LH82)(Zx8 x QH101 | 7.41 |
| IA1 | LH192SDms x LH82(*Zx9 x QH101 | 6.71 |
| IA1 | LH195SDms x LH59)(Zx1 x QH101 | 5.94 |

-continued

| Location | Pedigree | % Oil (db) |
|---|---|---|
| IA1 | LH195SDms x LHS9)(Zx15 x QH101 | 6.16 |
| IA1 | LH195SDms x LH59)(Zx16 x QH101 | 5.59 |
| IA1 | LH195SDms x LH59)(Zx2 x QH101 | 5.99 |
| IA1 | LH195 SDms x LH59)(Zx3 x QH101 | 5.65 |
| IA1 | LH195SDms x LH59)(Zx8 x QH101 | 6.17 |
| IA1 | LH195SDms x LH59)(Zx9 x QH101 | 5.93 |
| IA2 | LH192SDms x LH82)(LH195 x QH101 @ 1 | 5.64 |
| IA2 | LH192SDms x LH82)(QH101 x @ 1 P22.2 @ 1 | 6.89 |
| IA2 | LH192SDms x LH82)(Zx13 x QH101 @ 1 | 6.6 |
| IA2 | LH192SDms x LH82)(Zx14 x QH101 @ 1 | 6.62 |
| IA2 | LH192SDms x LH82)(Zx7 x QH101 @ 1 | 6.19 |
| IA2 | LH195SDms x LHS9)(QH101 x @ 1 P22.2 @ 1 | 6.31 |
| IA2 | LH195SDms x LHS9)(Zx13 x QH101 @ 1 | 5.62 |
| IA2 | LH195SDms x LH59)(Zx14 x QH101 @ 1 | 5.99 |
| IA2 | LH195SDms x LH59)(Zx7 x QH101 @ 1 | 5.9 |
| IN | LH192SDms x LH82)(Zx13 x QH101 @ 1 | 6.65 |
| IN | LH192SDms x LH82)(Zx14 x QH101 @ 1 | 7.03 |
| IN | LH195SDms x LH59)(Zx13 x QH101 @ 1 | 6.17 |
| IN | LH195SDms x LH59)(Zx14 x QH101 @ 1 | 5.65 |
| IN | LH200 x LH283)(QH101 x P22.2 @ 1 | 6.3 |
| IN | LH200 x LH283)(Zx13 x QH101 @ 1 | 6.49 |
| IN | LH200 x LH283)(Zx14 x QH101 @ 1 | 6.2 |
| IN | LH200 x LH283)(Zx7 x QH101 @ 1 | 6.22 |
|  | Low Oil Hybrid x Low Oil Hybrid |  |
| IA2 | LH192SDms x LH82)(LH195 x LH185 @ 1 | 4.57 |
| IA2 | LH192SDms x LH82)(LH195 x LH2126 @ 1 | 4.67 |
| IA2 | LH192SDms x LH82)(LH195 x LH262 @ 1 | 4.87 |
| IA2 | LH195SDms x LH59)(LH195 x LH185 @ 1 | 4.43 |
| IA2 | LH195SDms x LH59)(LH195 x LH216 @ 1 | 4.54 |
| IA2 | LH195SDms x LH59)(LH195 x LH262 @ 1 | 4.49 |
| IN | LH192SDms x LH82)(LH195 x LH185 @ 1 | 4.52 |
| IN | LH192SDms x LH82)(LH195 x LH216 @ 1 | 4.70 |
| IN | LH200 x LH283)(LH195 x LH185 @ 1 | 4.69 |
|  | Low Oil Hybrids |  |
| IA2 | LH195 x LH185 @ 1 85587 IT96 | 4.16 |
| IA2 | LH195 x LH216 @ 1 85590 IT96 | 4.53 |
| IA2 | LH195 x LH262 @ 1 85593 IT96 | 4.37 |
| IN | LH195 x LH185 @ 1 6482 IN96 | 4 |
| IN | LH195 x LH216 @ 1 6486 IN96 | 3.77 |

The data in Table 1 demonstrate that QH101 can be used, either singly or in combination, to produce a pollinator corn plant which produces high oil corn grain on low oil corn hybrids. Typically, field corn grain possess oil contents of between 3.5–4.5% (db) as illustrated by grain arising on typical Low Oil Hybrids (self pollination) and Low Oil× Low Oil Hybrids (Table 1). The ability of QH101 to increase the oil content of grain arising on a low oil hybrid is evident in the cross:

| Pedigree | Oil (%, db) |
|---|---|
| LH192SDms × LH82)(LH195 × QH101 @ 1 | 5.64 |

Varieties which are hybrids among QH101 and other high oil sources such as ZX and P22, raise the oil content of grain produced on low oil hybrids even higher when used as pollinators. This example illustrates that QH101 was used in a variety of material combinations to raise the content of oil in grain arising on low oil hybrids when these QH101 derivatives are used as pollinators in a nursery test simulating grain composition realized in the TopCross® grain production system.

EXAMPLE 2

Grain Harvested from QH101 Hybrid Corn Plants Contains Elevated Levels of Oil The inbred line QH101 contributes the attribute of elevated oil content when it is used as a parent line in corn hybrids. To demonstrate the effect of elevated oil content, several corn hybrids were prepared by mating common commercial female inbred lines with the inbred line QH101, growing the resulting corn hybrids in field nursery plots during the summer of 1996, producing grain on said hybrid plants through sib-mating via hand-pollination, and measuring the oil content of said grain produced using near-infrared transmission analytical instrumentation calibrated to measure oil content in corn grain. Each of these methods are common procedures well known by those skilled in the art of corn breeding. Eleven different hybrids were produced using QH101 as the male inbred parent, mated to eleven different typical commercial female corn inbred lines. These hybrids were raised and grain produced at two to seven different field locations in the central United States during the 1996 growing season. For comparison, the same eleven typical commercial female corn inbred lines were also used to produce eleven typical dent corn hybrids using typical commercial male corn inbred lines. These typical hybrids are referred to as check hybrids. Grain was produced from these check hybrids in the same manner as previously described for the QH101 hybrids. These check hybrids were raised and grain produced at two to 27 different locations in the central United States during the 1996 growing season.

The results of the grain analysis demonstrate that hybrids produced with QH101 as the male inbred parent contain one to two percentage points higher oil content, expressed on a dry matter basis, than typical dent corn hybrids.

| | | Check Hybrids | | QH101 Hybrids | |
|---|---|---|---|---|---|
| Female Inbred | Male Inbred | Avg Oil Content* | Number of Samples | Avg Oil Content* | Number of Samples |
| LH195 | LH172 | 4.40 | 18 | 6.15 | 7 |
| LH198 | LH168 | 4.41 | 25 | 5.99 | 5 |
| LH199 | LH216 | 4.63 | 6 | 6.00 | 4 |
| LH200 | LH172 | 4.68 | 27 | 6.11 | 7 |
| LH227 | LH172 | 4.09 | 8 | 6.18 | 2 |
| LH231 | LH172 | 4.49 | 13 | 6.13 | 3 |
| LH233 | LH172 | 4.50 | 5 | 6.26 | 4 |
| LH234 | LH172 | 4.77 | 18 | 5.79 | 4 |
| LH235 | LH210 | 4.16 | 11 | 5.97 | 6 |
| LH236 | LH216 | 4.21 | 2 | 5.95 | 5 |
| LH74 | LH172 | 4.35 | 15 | 6.52 | 3 |

*Oil content expressed on a zero percent moisture basis.

On average, the check typical hybrids had oil content of 4.43%, consistent with standards in the industry which assume oil content of dent corn to be 4.0%. The QH101 hybrids produced grain with an average 6.10% oil content, substantially above the oil content observed for typical dent corn.

DEPOSIT INFORMATION

Inbred seeds of QH101 have been placed on deposit with the American Type Culture Collection (ATCC), Rockville, Md. 20852, under Deposit Accession Number 97821 on Dec. 6, 1996.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Inbred corn seed designated QH101 having ATCC accession No. 97821.
2. A corn plant produced by growing the seed of claim 1.
3. Pollen of the plant of claim 2.
4. An ovule of the plant of claim 2.
5. An inbred corn plant capable of expressing all the physiological and morphological characteristics of the corn plant of claim 2.
6. A tissue culture comprising regenerable cells of the plant of claim 2.
7. A corn plant regenerated from said tissue culture of claim 6, wherein said corn plant is capable of expressing all the physiological and morphological characteristics of the corn plant of claim 2.
8. A method to produce a hybrid corn seed comprising the steps of:

a) planting in pollinating proximity seeds of corn inbred line QH101 having ATCC NO. 97821 and another inbred line;

b) cultivating corn plants resulting from said seeds until said plants bear flowers;

c) emasculating the male flowers of the plants of either inbred line;

d) allowing cross pollination to occur between said inbred lines; and, e) harvesting seeds produced on said emasculated plants of the inbred line.

9. A first generation ($F_1$) hybrid corn plant produced by growing said hybrid corn seed of claim 8.
10. Seed derived from the hybrid corn plant of claim 9.

* * * * *